United States Patent [19]  
Taniyama et al.

[11] Patent Number: 4,968,674  
[45] Date of Patent: Nov. 6, 1990

[54] ANTIVIRAL CARBOCYCLIC PURINE NUCLEOSIDES

[75] Inventors: Yoshio Taniyama, Osaka; Takumi Hamana, Hyogo; Ryuji Marumoto, Okuikeminami; Naoki Yamamoto, Yamaguchi, all of Japan

[73] Assignee: Takeda Chemical Industries, Ltd., Osaka, Japan

[21] Appl. No.: 22,014

[22] Filed: Mar. 5, 1987

[30] Foreign Application Priority Data

Mar. 6, 1986 [JP] Japan .................................. 61-49395  
Feb. 5, 1987 [JP] Japan .................................. 62-25074

[51] Int. Cl.$^5$ .................... A61K 31/52; C07D 473/16; C07D 473/18
[52] U.S. Cl. .................................... 514/63; 514/261; 514/262; 514/263; 514/258; 514/303; 544/254; 544/265; 544/267; 544/276; 544/277; 544/279; 546/118
[58] Field of Search ............... 544/265, 277, 276, 267, 544/229; 514/263, 63, 261, 262

[56] References Cited

U.S. PATENT DOCUMENTS

| | | | |
|---|---|---|---|
| 3,917,837 | 11/1975 | Lin et al. | 514/261 |
| 4,543,255 | 9/1985 | Shealy, et al. | 514/258 |
| 4,605,659 | 8/1986 | Verheyden et al. | 514/262 |
| 4,782,062 | 11/1988 | Tolman et al. | 514/262 |
| 4,916,224 | 4/1990 | Vince et al. | 544/254 |

FOREIGN PATENT DOCUMENTS 50-62992 5/1975 Japan .  
60-215685 10/1985 Japan .

OTHER PUBLICATIONS

Symposium Series 16 1985, *Nucleic Acids Research*, pp. 141–142, Miyashita et al.
Santi et al., "Phenylalanyl Transfer Ribonucleic Acid Synthetase from *Escherichia Coli*. Analysis of the Adenosine Triphosphate Binding Site", *Biochemistry*, vol. 10, No. 25, pp. 4821–4824, 1971.
Coward et al., "Analogs of S-Adenosylhomocysteins as Potential Inhibitors of Biological Transmethylation. Specificity of the S-Adenosylhomocysteine Binding Site", *J. Medicinal Chemistry*, vol. 16, No. 5, pp. 460–463, May 1973.
Chemical and Pharmaceutical Bulletin, vol. 24, 2624–2628 (1976), Marumoto et al.
Journal of Medical Chemistry, 1986, vol. 29, No. 9, 1561–1569, DeClereq.
Proc. Natl. Acad. Sci. U.S.A. 83 (1986), pp. 1911–1915, Mitsuya et al.
Marquez et al., Biochemical Pharmacology, vol, 36, No. 17, pp. 2719–2722 (1987).
York, J. Org. Chem., vol. 46, No. 10, pp. 2171–2173 (1981).
Drayer, et al., Clinical Pharmacology & Therapeutics, vol. 40, No. 3, pp. 125–133 (08/86).
Kato et al., Yakabutu Doutai(pharmokinetics), vol. 2, No. 2, pp. 171–182 (1987).
Schaeffer et al., J. Pharm. Sci., vol. 53, No. 12, pp. 1510–1515 (12/64).
Marquez et al., "Carbocyclic Nucleosides", Medicinal Research Reviews, vol. 6, No. 1, pp. 1–8, 11–16 and 37–40 (1986).
Montgomery et al., J. Am. Chem. Soc., vol. 80, pp. 409–411 (1958).
Shealy et al., Chemical Abstracts, vol. 71:81310s (1969.
Shealy et al., Chemical Abstracts, vol. 101:192384b (1984).
Miyashita et al. Chemical Abstracts, vol. 106:84996x (1987), abstract of Japan 60,215,685, 10/29/85.

*Primary Examiner*—Diana G. Rivers  
*Attorney, Agent, or Firm*—Wegner & Bretschneider

[57] ABSTRACT

A compound of the formula:

$$\begin{array}{c} R-6' \quad 5' \quad Y \\ 4' \qquad \quad 1' \\ 3' \qquad 2' \end{array}$$

wherein R is a hydroxyl group which may be protected and Y is a purine base which may be protected, and the saltts thereof, which are useful as an antiviral agent.

7 Claims, No Drawings

ANTIVIRAL CARBOCYCLIC PURINE NUCLEOSIDES

This invention provides nucleoside analogs having a cyclopentane ring which can be used as substitutes for purine nucleosides in the fields of biology, medicine or gene manipulation and as antiviral agents.

Derivatives of the compounds having the formula

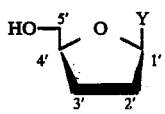

wherein Y is guanin-9yl or adenin-9-yl are the examples of dideoxy analogs of purine nucleosides used in determination of base sequences in DNA [Proc. Nat. Acad. Sci. USA, 74,4563 (1977)]. However 2′,3′-dideoxy analogs of purine nucleosides are so susceptible to acids that cleavage occurs easily at the glycosyl linkage, which is a great difficulty in their synthesis.

Recently it has been reported that 2′,3′-dideoxy analogs of purine nucleosides can act as inhibitors of reverse transcriptase of virus origin, and hence these analogs have attracted attention as therapeutics in diseases due to RNA virus [Chemical and Engineering News, Jan. 27, No. 28 (1986)].

Although, as mentioned above, dideoxy nucleosides and their carbocyclic analogs have been studied to some extent, there are still many aspects to be clarified. Therefore it is important to synthesize and evaluate various analogs. This invention intends to provide novel 2′,3′-dideoxycarbocyclic nucleosides which can be used as antiviral agents or for other purposes.

The inventors completed this invention as the result of their researches under the circumstances described above to obtain novel and useful purine nucleoside analogs. Thus, this invention relates to (1) A compound of the formula (I)

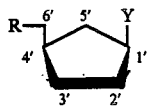

wherein R is a hydroxyl group which may be protected and Y is a purine base which may be protected, and the salts thereof, (2) a method of production of the compounds having the formula (I) and the salts thereof, which comprises subjecting a compound of the formula (II)

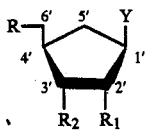

wherein R is a hydroxyl group which may be protected, either $R_1$ or $R_2$ is a hydroxyl group and the other is a hydrogen, and Y is a purine base which may be protected, to reduction reaction of the 2′ or 3′-hydroxyl group, and (3) an antiviral agent containing a compound of the formula (I).

The protective groups of the hydroxyl group in the compounds of the formula (I) or (II) are not specifically limited as far as they are those used as protective groups in nucleoside chemistry. In this invention the protective groups which are relatively stable under alkaline conditions are advantageously used, such as alkylsilyl groups having 3-10 carbon atoms (e.g. t-butyldimethylsilyl), alkyl or alkoxy cyclic ethers having 4-10 carbon atom (e.g. tetrahydrofuranyl and its derivatives having 4-7 carbon atoms, tetrahydropyranyl and its derivatives having 5-8 carbon atoms such as methoxytetrahyropyranyl), alkoxyalkyl groups having 3-10 carbon atoms (e g. ethoxyethyl, methoxyethyl), and trityl and its derivatives substituted with mono or dialkoxy having 1 or 2 carbon atoms (e.g. monomethoxytrityl, dimethoxytrityl). When the protective group is an acyl group, the hydroxyl group can be protected in the form of an aliphatic acid ester (e.g. straight chain or branched with 1-10 carbon atoms), arylcarboxylic acid ester (e.g. with 5-30 carbon atoms)

Purine bases represented by Y include various bases having a purine ring skeleton which are used usually in the field of nucleic acid chemistry. Such bases are exemplified by adenine, hypoxanthine, guanine, isoguanine, xanthine, 3-deazaadenine, 7-deazaadenine, 8-azaadenine, and 2,6-diaminopurine, and bound via the nitrogen atom at 9 position in the purine ring of the compound having the formula (I) or (II).

The protective group of the purine base in a compound of the formula (I) or (II), i.e. the amino protective group at the 2 or 6-position is any of those which can be used usually in the field of nucleoside chemistry. For example an arylcarboxylic acid residue (with 5-30 carbon atoms) such as benzoyl for a protective group of adenine and an aliphatic carboxylic acid residue (straight chain or branched, with 2-10 carbons e.g., isobutyryl oracetyl,) for a protective group of guanine are favorably used For production of a compound of the formula (I) from a compound of the formula (II), the hydroxyl group at the 2′ or 3′-position in a compound of formula (II) is thiocarbonylated at 0°-80° C. or preferably at room temperature, followed by reduction with tributyl tin hydride in the presence of an equivalent amount or an excess of α,α′-azobisisobutylonitorile at 0°-100° C. for 30 minutes to 2 hours, to give a 2′,3′-dideoxy derivative having the formula (I). The thiocarbonylation can be favorably conducted by using thiocarbonyl diimidazole for thiocarbonylation, phenyl chlorothiocarbonate for phenoxythiocarbonylation. Further, S-methyldithiocarbonylation may be carried out also by using the mixture of carbon bisulfide and methyl iodide. After this reduction, the 6′hydroxyl protective group, for example, the 4,4-dimethoxytrityl group is easily removed under acidic condition (e.g treatment with acetic acid or IN hydrochloric acid at room temperature), and moreover the protective group of purine base can be removed under alkaline condition (e.g. concentrated ammoniac water, 1N-sodium hydroxide, 1M-sodium ethylate).

The compounds of formula (II) can be produced by, for example, the following procedure: the compounds of formula (II) of which Y is an adenin-9-yl, which may be protected, can be produced also by the method described in Japanese Patent Application Laid-Open No. 62992/1975, Chemical & Pharmaceutical Bulletin 24,2624(1976) or Nucleic Acids Symposium Series, No.16,141(1985). For example by the method described in Japanese Patent Application Laid-Open No. 62992/1975 or Chemical & Pharmaceutical Bulletin 24,2624(1976), a compound in which in the formula (II) Y is adenin-9-yl, either $R_1$ or $R_2$ is a hydroxyl group and the other is a hydrogen, and R is a hydroxyl group is obtained by using aristeromycin as starting compound; and a compound in which Y in the formula (II) is $N^6$-benzoyl-adenin-9-yl, R is a hydroxyl group protected with 4,4'-dimethoxytrityl, and $R_1$ is a hydrogen and $R_2$ is a hydroxyl group is obtained by the method described in Nucleic Acids Symposium Series described above A compound in which Y in the formula (II) is guanin-9-yl or hypoxanthin- 9-yl which may be protected, R is a hydroxyl group which may be protected, with a hydrogen at 2'-position and a hydroxyl group at 3'-position is obtained by the method described in Japanese Patent Application No. 236858/1985 and the corresponding U.S. patent application Ser. No. 920,116 (see the Reference Examples 1-8)

On the other hand, the compound of formula (II) in which Y is 2,6-diaminopurine-9-yl, $R_1$ is hydrogen, $R_2$ is a hydroxyl group can be synthesized as follows: The hydroxyl group of the compound in which Y is adenin9-yl is protected, followed by N1-oxidation with hydrogen peroxide or metachloro perbenzoic acid, and then the amino group at 6-position is deaminated by nitrous acid, and the product is heated with phosphorus oxychloride (Japanese Patent Publication No. 4347/1967) to give the corresponding 2,6-dichloropurine-9-yl derivative. The chlorine at 6-position is substituted by an amino group, and deamination is conducted by using sodium nitrite in aqueous acetic acid to give the product of 2-chloro-6-hydroxyl-9-yl. The compound obtained is subjected to amidation at the 2-position and after chlorination at the 6-position, the chlorine at this position is substituted by an amino group to give the desired compound.

The salts of the compounds having the formula (I) in this invention include those formed with the amino group in the purine base and a mineral acid (e.g. hydrochloric acid, sulfuric acid, nitric acid), an organo carboxylic acid (e.g. acetic acid, lactic acid, tartaric acid, maleic acid, succinic acid) or an organesulfonic acid (e.g. methanesulfonic acid, ethansulfonic acid, benzenesulfonic acid).

The compounds of the formula (I) in this invention provide useful tools in gene cloning. That is, the analogs derived from the compounds of this invention having cyclopentane ring are the carbocyclic analogs of purine-2',3'-dideoxynucleotide, and are easily synthesized because of absence of a glycosyl linkage, and the triphosphate derivatives thereof may be used as agents to stop the DNA chain elongation in determination of DNA sequence.

On the other hand, the compounds of the formula (I) have antiviral activity against DNA viruses or RNA viruses. There may be mentioned as DNA viruses herpesvirus group (e.g. herpes simplex virus type I or II, cytomegalovirus, Epstein-Barr virus), adenovirus (e.g. type III), Hepatitis B virus or poxvirus; as RNA viruses human immunodeficiency virus(HIV), which is a pathogen of acquired human immunodeficiecy virus (AIDS), vesicular stomatitis virus, feline leukemia virus, equine infectious anemic virus. Especially, the compounds of the present invention have potent antiviral activity against RNA viruses, in particular HTLV-III(-Human T-cell Lymphotropic virus type III, $HIV_{HTLV-III}$), which in one of HIV, as possible inhibitors of reverse transcriptase.

Accordingly, the compounds of the present invention may be used for treatment against various viral infections. As such viral infections, there may be mentioned acquired immunodeficiency syndrome; herpes simplex (type I or II), varicella, zoster, keratitis, conjunctivitis or acute hepatitis various opportunistic infections, malignant tumor or central nervous symptoms which are brought out by viral infection and immunodeficiency.

The compounds of the formula (I) and the pharmaceutically acceptable salts thereof can be also used as antiviral agents for treatment of virus-induced disease in animals, particularly in mamalian animals (laboratory animals such as rabbit, rat and mouse; pet animals such as dog and cat; human being; livestock such as cattle, horse, sheep and pig).

In general for the above purpose, a suitable effective dose of the compounds of the present invention is in the range of 30–500 mg per kg body weight per day, preferably in the range of 100–300 mg per kg body weight per day. The desired dose is generally presented as two, three or four more sub-doses administered at appropriate intervals throughout the day. Administration may be any suitable route including oral, rectal, nasal, topical (e.g. buccal, sublingual), vaginal and parenteral (e.g. subcutaneous, intramuscular, intravenous, intradermal). The preferred route may vary with, for example, the condition and age of the recipient. While the present compounds can be administered alone, it is preferable to present them as part of pharmaceutical formulation. The formulations of the present invention comprise at least one of the compounds of the formula (I), together with one or more acceptable carrier thereof and optionally other therapeutic ingredients.

The formulation may conveniently be presented in unit dosage form. Formulations containing the compound of the present invention for oral administration include discrete units such as capsules or tablets; powder or granules; solution or suspension; or an oil-in-water liquid emulsion or a water-in-oil liquid emulsion etc.

A tablet may be made by compression or molding, optionally with one or more accessory ingredients. Compressed tablets may be prepared by compressing in a suitable machine the compound of the present invention in a form of a powder or granules, optionally mixed with a binder (e.g. hydroxypropyl-cellulose), lubricant (e.g. magnesium stearate), inert diluent (e.g. starch), preservative, surface-active or dispersing agent.

Formulations for parenteral administration include aqueous and non-aqueous sterile injection solutions which may contain anti-oxidants, buffers or, bacteriostats; and aqueous and non-aqueous sterile suspensions which may include suspending agents and thickening agents The formulations may be presented in unit-dose or multi-dose containers, for example, sealed ampules and vials, and may be stored in a freeze-dried condition requiring only the addition of the sterile liquid carrier, for example water for injections, immediately prior to use. Extemporaneous injection solutions and suspensions may be prepared from sterile powders, granules and tablets.

Formulations for topical administration include lozenges comprising the present compounds in a flavoured form, usually sucrose and acacia or tragacanth; pastilles comprising the present compound in an inert basis such as gelatin and glycerin, or sucrose and acacia; and monthwashes comprising the ingredient to be administered in a suitable liquid carrier.

Formulations for rectal administration may be presented as a suppository with a suitable base such as cacao butter.

Formulations for vaginal administration may be presented as pessaries, tampons, creams, gels, pastes, foams or spray formulations containing in addition to the present compound such carriers as are known in the art to be appropriate.

Among the compounds of the formula (I), particularly 2′,3′-dideoxyaristeromycin (the compound of Example 3) and 9-[(1S,4R)-4-hydroxymethylcyclopentan-1-yl]guanine (the compound of Example 4) inhibit potently growth of AIDS virus, and they are more useful compounds accordingly.

In the following, Reference Examples, Examples and Test Example are presented by which the invention is explained in detail.

REFERENCE EXAMPLE 1

Synthesis of 9-[(1R,2S,3R,4R)-4-methyl-2-hydroxyl3,6-(tetraisopropyldisiloxanyl)dioxycyclopentan-1-yl]hypoxanthine The C-analog to inosine (10 g, 37.5 mmol) was dissolved in 200 ml of anhydrous DMF, 1,3-dichloro1,1,3,3-tetraisopropyldisiloxane (13 ml, 41 mmol) and imidazole (11.3 g, 165 mmol) were added, and the mixture was stirred at room temperature for 2.5 hours. The reaction mixture was added dropwise to 2 liters of water, and the precipitate was collected by filtration, washed with water, further washed quickly with diethyl ether and dried to give the title compound as a white powder (17.2 g). A portion of the product was recrystallized from dichloromethane to give crystals, m.p. 135°–138° C.

Note: The C-analog to inosine is known by Chemical & Pharmaceutical Bulletin 24, 2624(1976).

REFERENCE EXAMPLE 2

Synthesis of 9-[(1R,2S,3R,4R)-4-methyl-2-phenoxythiocarbonyloxy-3,6-(tetraisopropyldisiloxanyl)dioxycyclopentan-1-yl]hypoxantine The compound obtained in Reference Example 1 (11.2 g, 22.3 mmol) was dissolved in 300 ml of anhydrous acetonitrile, dimethylaminopyridine (15.8 g, 53.5 mmol) and phenoxythiocarbonyl chloride (5 g, 29 mmol) were added and the mixture was stirred at room temperature for 7 hours. The solvent was removed under reduced pressure, and the residue was dissolved in 250 ml of chloroform. The solution was washed with 0.5 M potassium dihydrogen phosphate solution (250 ml×2) and then with water (200 ml), dried (anhydrous sodium sulfate) and concentrated under reduced pressure to give a yellow syrup. This was purified by silica gel chromatography (90 g; solvent: $CHCl_3$ and $CHCl_3$/ MeOH=60/1) to give the title compound as a light-yellow grass-like substance (13.0 g).

NMR(60MHz,$CDCl_3$)δppm: 1.0–1.23 (28H, m), 2.13–2.43 (3H, m, $H_4'$, $H_5'$), 3.93–4.10 (2H, m, $H_6'$), 4.80–5.20 (2H, m, $H_1'$, $H_3'$), 6.00–6.20 (H, m, $H_2'$), 7.03–7.50 (5H, m), 7.87 (1H, s), 8.13 (1H, s) s;singlet, m;multiplet

REFERENCE EXAMPLE 3

Synthesis of 9-[(1R,3S,4R)-4-methyl-3,6-(tetraisopropyldisiloxanyl)dioxycyclopentan-1-yl]hypoxanthine Anhydrous toluene (30 ml) was added to the compound obtained in Reference Example 2 (13.0 g, 20 mmol), followed by concentration under reduced pressure. The residue was dissolved in 300 ml of anhydrous toluene, and nitrogen gas was bubbled into the solution for 20 minutes. After addition of tributyltin hydride (11 ml, 40 mmol) the solution was heated at 80° C. and crystalline α, -α′-azobisisobutyronitrile (AIBN) (820 mg) was added in 4 portions at 15-minute intervals. After 3 hours of heating with stirring, the solvent was removed under reduced pressure. The oil obtained was purified by silica gel chromatography (80 g; solvent: $CHCl_3$ and $CHCl_3$/ MeOH=60/1 to 30/1) to give the title compound as a colorless glass-like substance (10.4 g). Recrystallization of a portion of the product from ethanol gave colorless needles, m.p. 200°–202° C.

NMR(60MHz,$CDCl_3$)δppm: 0.93–1.20 (28H, s), 1.97–2.53 (5H, m, $H_2'$, $H_4'$, $H_5'$), 3.80–4.07 (2H, m, $H_6'$), 4.43–5.27 (2H, m, $H_1'$, $H_3'$), 7.87 (1H, s), 8.20 (1H, s)

REFERENCE EXAMPLE 4

Synthesis of 9-[(1R,3S,4R)-4-(monomethoxytrityloxy)-methyl-3-hydroxylcyclopentan-1-yl]-(1-methoxymethylhypoxantine)

The compound obtained in Reference Example 3 (9.8 g, 19.8 mmol) was dissolved in 240 ml of anhydrous dioxane, sodium hydride (880 mg, 21.8 mmol) was quickly added to the solution with ice cooling and stirring and, then, the mixture was stirred at room temperature for 1.5 hours. Thereafter, methoxymethyl chloride (2 ml, 21.8 mmol) was quickly added to the mixture with ice cooling. The whole mixture was stirred at room temperature for 3 hours.

The solvent was removed under reduced pressure and the oily residue was dissolved in 200 ml of chloroform. The solution was washed with 0.1 M triethylammonium bicarbonate (TEAB) buffer (pH 7.5, 100 ml×2) and further with water (200 ml), dried (anhydrous sodium sulfate) and concentrated under reduced pressure to give a syrup. Purification of the syrup by $C_{18}$ silica gel chromatography (φ5.3×7.0 cm; solvent:acetone water, 55%–80%) gave a colorless glass-like compound (8.5 g).

This compound (8.0 g) was dissolved in 32 ml of tetrahydrofuran (THF), tetrabutylammonium fluoride trihydrate (TBAF.3$H_2O$) (10 g) was added, and the mixture was stirred at room temperature for 0.5 hour. The solvent was removed under reduced pressure and the remaining oil was dissolved in 100 ml of water. The solution was washed with diethyl ether (100 ml×2) and was deprived of the tetrabutylammonium salt by treatment on Dowex-50 resin (pyridine form 60 ml). The effluent and water washings (240 ml) were combined and concentrated and the concentrate was dehydrated azeotropically with three portions of pyridine. The residue was dissolved in 100 ml of pyridine, monomethoxytrityl chloride (MMTrCl) (5.4 g) was added and the mixture was stirred at 37° C. for 4 hours. The solvent was removed under reduced pressure and the oily residue was distributed between 0.1M TEAB buffer (50 ml) and $CHCl_3$ (100 ml), the organic layer was washed with water (100 ml), dried (anhydrous sodium sulfate) and concentrated under reduced pressure and the concentrate was subjected to dehydration by azeotropic distillation with toluene to give a colorless syrup. 0.1 M-TEAB buffer fraction and water washings were combined and concentrated, whereby the unmonomethoxytritylated compound was recovered. This compound was purified on HP-20 resin (190 ml; solvent: water and 30% ethanol-water) and, after concentration and azeotropic distillation with pyridine, monomethoxytritylated in the same manner as mentioned above. Both the thus-obtained crops of the title compound were combined and purified by silica gel chromatography (80 g; solvent: $CHCl_3/MeOH = 100/1, 60/1, 50/1$) to give a colorless glass-like product (6.1 g). A solution of a portion of this product in dichloromethane, when added dropwise to n-hexane, gave a white powder.

NMR(60 MHz,$CDCl_3$)δ ppm: 1.87–2.70 (5H, m, $H_2'$, $H_4'$, $H_5'$), 3.20–3.40 (2H, m, $H_6'$), 3.43 (3H, s, $CH_3OCH_2$), 3.80 (3H, s), 4.30–4.57 (1H, m, $H_3'$), 4.87–5.10 (1H, m, $H_1'$), 5.47 (2H, s, $CH_3OCH_2N$), 6.73–6.97 (2H, m), 7.17–7.53 (12H, m), 7.73 (1H, s), 7.98 (1H, s)

REFERENCE EXAMPLE 5

Synthesis of 1-[(1R,3S,4R)-4-(monomethoxytrityloxy)methyl-3-hydroxycyclopentan-1-yl]-(4-carbamoyl-5-aminoimidazole)

The compound obtained in Reference Example 4 (6.1 g, 10.7 mmol) was dissolved in 490 ml of ethanol and, with heating under reflux, a warmed 5 M aqueous sodium hydroxide solution (130 ml) was added quickly. Refluxing was continued for additional 40 minutes. The solvent was then removed under reduced pressure. The oily residue was dissolved in 200 ml of chloroform and washed with water (100 ml×2), then with 0.1 M-TEAB buffer (100 ml×2) and further with saturated aqueous sodium chloride solution (100 ml), dried (anhydrous sodium sulfate) and concentrated under reduced pressure to give a syrup. Purification of this syrup by silica gel chromatography (90 g; solvent: $CHCl_3/MeOH = 100/1$ to $20/1$) gave a colorless glass-like product (3.2 g). A solution of a portion of this product in chloroform, when added dropwise to n-pentane with stirring, gave a white powder.

Elemental analysis (%) for $C_{30}H_{32}N_4O_4 \cdot 0.5\ H_2O$, molecular weight 521.616

Calculated : C, 69.08; H, 6.38; N, 10.74
Found C, 69.14; H, 6.09; N, 10.54
NMR(100MHz,$CDCl_3$)δ ppm: 1.36–2.52 (5H, m), 3.00–3.40 (3H, m, $H_6'$, OH), 3.77 (3H, s), 4.12–4.60 (2H, m, $H_1'$, $H_3'$), 4.80–5.28 (2H, bs, $NH_2$), 5.64–6.44 (2H, bs, $NH_2$), 6.76–6.94 (3H, m), 7.14–7.48 (12H, m) bs;broad singlet

REFERENCE EXAMPLE 6

Synthesis of 1-[(1R,3S,4R)-4-(monomethoxytrityloxy)methyl-3-hydroxycyclopentan-1-yl]-[4-carbamoyl-5-(N-benzoyl-S-methylisothiocarbamoyl)aminoimidazole]

The compound obtained in Reference Example 5 (0.88 g, 1.7 mmol) was dissolved in 25 ml of anhydrous acetone and, with heating under reflux, a solution of benzoyl isothiocyanate (260μl, 1.9 mmol) in acetone (8 ml) was added dropwise over 10 minutes, followed by refluxing for 50 minutes. The solvent was removed under reduced pressure and the light-yellow glass-like substance obtained was purified by silica gel chromatography (15 g; solvent: $CHCl_3/MeOH = 50/1$ to $30/1$) to give a light-yellow glass-like compound (0.87 g). A small amount of acetone was added to this compound (0.84 g, 1.2 mmol) and the resultant syrup was converted to a homogeneous solution by addition of 12.5 ml of 0.2 N NaOH and sonication. Dimethyl sulfate (130 μl 1.4 mmol) was added with stirring and, then, vigorous stirring was continued at room temperature for 1 hour. The reaction mixture was mixed with $CHCl_3$ (15 ml×2) for partition, the organic layer was washed with 0.1M TEAB buffer (15 ml×3) and then with saturated aqueous sodium chloride solution (20 ml), dried anhydrous sodium sulfate) and concentrated under reduced pressure, and the residue was purified by silica gel chromatography (15 g; solvent: $CHCl_3/MeOH = 100/1$ to $60/1$). A small amount of dichloromethane was added to the glass-like substance obtained, the mixture was added dropwise to hexane and the resultant precipitate was collected by centrifugation and dried to give the title compound as a powder (400 mg).

Elemental analysis (%) for $C_{39}H_{39}N_5O_5S$, molecular weight 689.835

Calculated : C, 67.90; H, 5.70; N, 10.15;
Found C, 67.45; H, 5.45; N, 9.89;
NMR(100MHz,$CDCl_3$)δ ppm: 1.34–2.60 (5H, m), 2.52 (3H, s, $SCH_3$), 3.04–3.44 (2H, m, $H_6'$), 3.79 (3H, s, $OCH_3$), 4.08–4.44 (1H, m, $H_3'$), 4.60–5.00 (1H, m, $H_1'$), 5.64 (1H, bs, $NH_2$), 6.72–6.94 (3H, m), 7.12–7.52 (15H, m), 7.80–7.96 (2H, m), 11.35 (1H, bs, NH)

REFERENCE EXAMPLE 7

Synthesis of 9-[(1R,3S,4R)-4-monomethoxytrityloxymethyl-3-hydroxycyclopentan-1-yl]guanine The compound observed in Reference Example 6 (360 mg, 0.53 mmol) was added to a warmed 6 N sodium hydroxide (18 ml) and the mixture was heated under reflux for 1 hour. The product was extracted from the reaction mixture with $CHCl_3$, and the extract was washed with 0.1 M TEAB buffer (30 ml) and then with saturated aqueous sodium chloride solution (30 ml), dried (anhydrous sodium sulfate) and subjected to silica gel chromatography (8 g; solvent: $CHCl_3$ MeOH = 40/1 to 6/1). To the thus obtained glass-like substance was added a small amount of acetone, the mixture was added dropwise to benzene and the resultant precipitate was collected by centrifugation and dried to give the title compound as a powder (210 mg).

Elemental analysis (%) for $C_{31}H_{31}N_5O_4 \cdot 1.0H_2O$, molecular weight 555.633

Calculated : C, 67.01; H, 5.99; N, 12.60
Found C, 67.01; H, 5.69; N, 12.42
NMR(100MHz,$DMSO-d_6$)δ ppm: 1.50–2.60 (5H, m), 3.01 (2H, bs), 3.98–4.20 (1H, m), 4.70–4.96 (2H, m), 6.37 (2H, bs, $NH_2$), 6.82–7.46 (14H, m), 7.68 (1H, s, $H_8$), 10.60 (1H, bs, NH)

REFERENCE EXAMPLE 8

Synthesis of 9-(1R,3S,4R)-4-hydroxymethyl-3-hydroxycyclopentan-1-yl]guanine

The compound obtained in Reference Example 7 (180 mg, 0.33 mmol) was dissolved in 10 ml of 80% acetic acid and the solution was stirred at 40° C. for 4.5 hours. The solvent was removed under reduced pressure and, further, azeotropic distillation was conducted twice with water. Water (10 ml) was added, the mixture was washed with ether (10 ml×2) and the water was removed under reduced pressure. Thus was obtained the title compound as colorless crystals (41 mg), m.p. 246–248° C.

$[\alpha]_D^{25} = +7.7°$ (C=0.5, DMF)
$\lambda_{max}$ (nm): ($H_2$ O); 255, 278 (sh);
($H^+$); 257, 282;
($OH^-$); 256 (sh), 273;

Elemental analysis (%) for $C_{11}H_{15}N_5O_3 \cdot 0.5H_2O \cdot 0.1 C_2H_5OH$, molecular weight 278.886
Calculated: C, 48.24; H, 6.00; N, 25.11
Found C, 48.61; H, 6.41; N, 25.40

EXAMPLE 1

$N^6$-benzoyl-6'-O-(4,4'-dimethoxytrityl)-3'-O-[(imidazol-1-yl)-thiocarbonyl]-2'-deoxyaristeromycin $N^6$-benzoyl-6'-O-(4,4'-dimethoxytrityl)-2'deoxyaristeromycin (2.5 g) was dissolved in 10 ml of dry dichloromethane, to which thiocarbonyl diimidazole (8.0 g) was added and stirred at room temperature for 20 hr. The reaction mixture was concentrated to dryness, and subjected to purification with silica gel chromatography (Kieselgel 60, Merck Co., 50 g, solvent:ethyl acetate), to give a light yellow glassy substance (yield 2.2 g).

NMR(90 MHz, CDCl$_3$) 6 ppm: 3.80 (6H,S,2 CH$_3$O), 8.35(1H,S,H$_8$), 8.76(1H,S,H$_2$).

EXAMPLE 2

$N^6$-benzoyl-6'-O-(4,4'-dimethoxytrityl)-2',3'-dideoxyaristeromycin

The 3'-thiocarbonyl derivative obtained in Example 1 (2.0 g) was dissolved in 20 ml of dry dioxane, to which a solution of tributyl tin hydride (4.5 g) in dry dioxane (10 ml) was added dropwise with refluxing by heating. Meanwhile crystals of α,α'-azobisisobutylonitorile (500 mg) were added little by little. The dropwise addition was completed in 20 minutes and refluxing was continued for further 2 hr. The solvent was evaporated off under reduced pressure, and the oily residue was purified with silica gel chromatography (40 g, solvent:CHCl$_3$), to give a colorless powder (1.1 g).

NMR(90MHz, CDCl$_3$) 6 ppm: 3.80 (6H,S,2 CH$_3$O—), 4.80–5.20 (1H, m, H$_{1'}$), 3.15 (2M, d, 2M$_{6'}$), 8.76(1H,S,H$_2$), 9.10

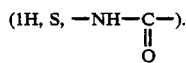
(1H, S, —NH—C—).
           ‖
           O

EXAMPLE 3

2',3'-dideoxyaristeromycin

The compound obtained in Example 2 (1.0 g) was dissolved in a small amount of pyridine, to which 50 ml of concentrated ammoniac water was added and heated in a pressure-proof tube at 60° C. for 5 hr. The reaction mixture was concentrated to dryness, to which 80% acetic acid (100 ml) was added and heated at 60° C. for 2 hr followed by concentration to dryness under reduced pressure. The residue was dissolved in water (100 ml) and washed twice with water. The aqueous layer was concentrated to dryness, and the residue was powderized in ether to give 2',3'-dideoxyaristeromycin (0.23 g).

Uv$\lambda_{max}^{H2O}$ (nm);260

Elemental analysis (%) for $C_{11}H_{15}N_5O \cdot H_2O$ with molecular weight 251.29
Calc.: C;52.57, H;6.82, N;27.87
Found: C;52.83, H;6.95, N;27.54

The thus obtained 2',3'-dideoxyaristeromycin was dissolved in the equivalent weight of 1N-HCl. After concentration, ethanol was added to the solution and concentrated to dryness. This procedure was repeated several times. The residue was recrystralized from hot ethanol to give the crystals of the hydrochloric acid salt. m.p. 173°–175° C.

Elemental analysis (%) for $C_{11}H_{15}N_5O \cdot HCl \cdot 1/2H_2O$ with molecular weight 278.73
Calc.: C;47.40, H;6.15, N;25.12, Cl;12.72
Found: C;47.98, H;6.06, N;24.87, Cl;12.71
$[\alpha]_D^{25} = -6.79(C=0.61, H_2O)$

EXAMPLE 4

The compound obtained in Reference Example 8 (2.5 g) was treated in as in Examples 1, 2, and 3, to give a crystalline powder of 9-[(1S,4R)-4-hydroxymethylcyclopentan-1-yl]-guanine (0.3 g). m.p. 269° C.

UV$\lambda_{max}^{pH2}$ (nm): 255,280(shoulder); UV$\lambda_{max}^{H-2O}$(nm):253,270 (shoulder); UV$_{max}^{pH10}$(nm): 258 (shoulder), 270

Elemental analysis (%) for $C_{11}H_{15}O_2N_5$ with molecular weight 249.27
Calc.: C;53.00, H;6.07, N;28.10
Found: C;52.81, H;5.86, N;27.83
$[\alpha]_D^{25} = -4.74(C=0.57, DMF)$ 9-[(1S,4R)-4-hydroxymethylcyclopentan-1-yl]hypoxanthine is obtained when a hypoxanthine derivative, instead of $N^6$-benzoyl-6'-O-(4,4'-dimethoxytrityl)-3'-O-[(imidazol-1-yl)-thiocarbonyl]-2'-deoxyaristeromycin in Example 1 is treated in a similar way to that in Examples 1–3.

Elementary analysis (%) for $C_{11}H_{14}N_4O_2$ with molecular weight 234.25
Calc.: C;56.40, H;6.02, N;23.92
Found: C;56.81, H;6.33, N;24.25

EXAMPLE 5

9-[1S,4R)-4-hydroxymethylcyclopentan-1-yl]guanine (1) Synthesis of 9-[(1R,3S,4R)-4-hydroxymethyl-3-hydroxylcyclopentan-1-yl]hypoxanthine The compound (12.4g, 20 m mol) obtained in Reference Example 3 was dissolved in 200 ml of toluene and to the mixture was added tetrabutylammonium fluoride (10.46 g, 40 m mol), followed by heating at 75° C. for 2 hr. The reaction solution was concentrated to dryness and dissolved in water. The solution was subjected to desaltation with 30 g of activated charcoal, the crude product was recrystallized from a mixture of methanol and ethylether to give colorless crystals (4.6 g). m.p. 170° C.

Elemental analysis (%) for $C_{11}H_{14}N_4O_3 \cdot H_2O$ with molecular weight 268.27
Calc.: C;49.25, H;6.01, N;20.88
Found: C;49.08, H;5.86, N;20.81

(2) Synthesis of 9-[(1R,3S,4R)-4-monomethoxytrityloxymethyl-3-hydroxylcyclopentan-1-yl]hypoxanthine The crystaline compound (2.3 g, 9.2 m mol) obtained by the method (1) described above was dissolved in 100 ml of pyridine, followed by addition of monomethoxytritylchloride (3.1 g, 10 m mol) and then was stirred at room temperature for 5 hr. The reaction solution was purified with silica gel chromatography (80 g, solvent: CHCl$_3$/MeOH=40/1-6/1) to give powdery desired product (4.3 g). A part of the product was recrystalized from a mixture of chloroform and ether. m.p. 244°–246° C.

Elementary analysis (%) for $C_{31}H_{30}N_4O_4 \cdot H_2O$ with molecular weight 531.60
Calc.: C;70.04, H;5.88, N;10.54
Found: C;70.39, H;5.77, N;10.38

(3) Synthesis of 9-[(1S,4R)-4-monomethoxytrityloxymethyl-cyclopentan-1-yl]hypoxanthine The compound (4.32 g, 8.27 m mol) obtained by the method (2) described above was dissolved in 70 ml of toluene, followed by addition of thiocarbonyldiimidazol (2.2 g, 12.4 m mol) and stirred at room temperature for 5 hr. The reaction solution was concentrated to dryness, and the residue was purified with silica gel chromatography (80 g, solvent: $CHCl_3/MeOH=100/1$–$60/1$) to give pale yellow powder (5.2 g). The thus obtained product was dissolved in 90 ml of toluene and reacted with tributyl tin hydride (3.4 ml, 12.4 m mol) and, $\alpha,\alpha'$-azobisisobutylonitrile (270 mg, 1.6 m mol) by the similar method as described in Reference Example 3, followed by purification with silica gel chlomatography (100 g, solvent: ethylacetate/MeOH=9/1) to give the desired product (1.63 g). A part of the product was recrystalized from a mixture solution of methanol and ethyl ether. m.p. 175–177° C.

Elementary analysis (%) for $C_{31}H_{30}N_4O_3 1/2H_2O$ with molecular weight 515.60

Calc.: C;72.21, H;6.06, N;10.87
Found: C;72.69, H;5.88, N;10.92 (4) Synthesis of 9-[(1S,4R)-4-hydroxymethylcyclopentan-1-yl]guanine The desired compound can be produced by methods as described in Reference Examples 4 to 8 using the compound obtained in the step (3) described above.

EXAMPLE 6

Tablets for oral administration of the antiviral composition according to the present invention are prepared as exemplified below:

Two hundred (200) mg of 2',3'-dideoxyaristromycin, 300 mg of lactose, 50 mg of starch and 2 mg of magnesium stearate are mixed in methanol and after removal of methanol with heating the mixture is molded into tablets.

EXAMPLE 7

An injectable antiviral composition is prepared as exemplified below:

Five hundred (500) mg of 2',3'-dideoxyaristeromycin is dissolved in 10 ml of sterilized water and adjusted to pH 6.0 with aqueous sodium hydroxide. The solution is filtered with sterilized filter and sealed up in vial.

TEST EXAMPLE 1

MATERIALS AND METHODS*

* Antimicrob Agents Chemother,30,No.6,Dec. 1986,933–937

Cells. An HTLV type I-carrying cell line, MT-4, and an $HIV_{HTLV-III}$-producing cell line, Molt-4/$HIV_{HTLV-III}$, were used in this study. The cells were maintained in RPMI 1640 medium supplemented with 10% fetal calf serum, 100 IU of penicillin per ml, and 100 μg of streptomycin per ml at 37° C. in a $CO_2$ incubator.

Virus and virus infection. $HIV_{HTLV-III}$ was obtained from culture supernatants of Molt-4/ $HIV_{HTLV-III}$ as previously described [Virology 146, 272(1985)]. The titer of this virus preparation was $6 \times 10^4$ PFU/ml. Infection of MT-4 cells with $HIV_{HTLV-III}$ was made at a multiplicity of infection of 0.002. Briefly, the cells were mixed with virus solution and incubated for 1 h at 37° C. After adsorption, infected cells were washed and resuspended in fresh medium to a concentration of $3 \times 10^5$ cells per ml. This concentration was cultured in both the presence and absence of various concentrations of carbocyclic 2',3'-dideoxynucleosides in a $CO_2$ incubator at 37° C. for 6 days.

Assay for $HIV_{HTLV-III}$-induced cytopathic effect. $HIV_{HTLV-III}$-induced cytopathic effect was analyzed by measuring the decrease in the number of viable cells. The viable cells were counted by the trypan blue exclusion staining method.

Assay for $HIV_{HTLV-III}$ antigen expression. $HIV_{HTLV-III}$-infected MT-4 cells with virus-specific antigens were counted by an indirect [immunofluorescence (IF)-]method. Briefly, methanol-fixed cells were incubated with diluted anti-$HIV_{HTLV-III}$ positive human serum for 30 min at 37° C. The preparations were then washed for 15 min with phosphate-buffered saline. The cells were then incubated with fluorescein isothiocyanate-conjugated rabbit anti-human immunoglobulin G (Dakoppatts A/S, Copenhagen, Denmark) for 30 min at 37° C. and washed again with phosphate-buffered saline. More than 500 cells were counted under a fluorescence microscope, and the percentage of IF-positive cells was calculated.

From the assay mentioned above, it was confirmed that the compounds of the present invention have obvious anti- $HIV_{HTLV-III}$ activity In the case of 2',3'-dideoxyaristeromycin, the effective concentration was 50–100 μM and the cytotoxity was observed at 500–1,000 μM, respectively

What we claim:

1. An optically pure compound of the formula:

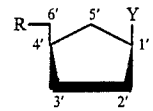

wherein
R is hydroxyl or hydroxyl protected by a protective group of the class consisting of an alkylsilyl having 3–10 carbon atoms, an alkyl ether having 4–10 carbon atoms, an alkoxy cyclic ether having 4–10 carbon atoms, an alkoxyalkyl having 3–10 carbon atoms, trityl, $C^{1-2}$-alkoxytrityl, and di($C^{1-2}$-alkoxytrityl); and Y is a purine base selected from the class consisting of adenin-9-yl, and 2,6-diaminopurin-9-yl, which can be protected by an aminoprotective group at the 2- or 6-position.

2. The compound according to claim 1, which is 9[(1S,4R)-4-hydroxymethylcyclopentan-1yl ]guanine.

3. The compound according to claim 1, wherein R is a hydroxy group protected with monomethoxytrityl or dimethoxytrityl group.

4. The compound according to claim 1, wherein the purine base is protected with benzoyl, isobutyryl or acetyl.

5. An antiviral composition which contains an effective anti-RNA-virus amount or an effective anti-hepatitis B virus amount of an optically pure compound of the formula:

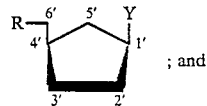 ; and wherein,
R is hydroxyl or hydroxyl protected by a protective group of the class consisting of an alkylsilyl having 3–10 carbon atoms, an alkyl ether having 4–10 carbon atoms, an alkoxy cyclic ether having 4–10 carbon atoms, an alkoxyalkyl having 3-10 carbon atoms, trityl, $C^{1-2}$-alkoxytrityl, and di($C^{1-2}$-alkoxytrityl), Y is selected from the class consisting of guanin-9-yl, and 2,6-diaminopurin-9-yl, which can be protected by an amino-protective group at the 2- or 6-position; and a pharmaceutically acceptable carrier.

6. The composition according to claim 5, wherein the RNA-virus is $HIV_{HTLV-III}$.

7. The composition according to claim 5, wherein the compound is 9-[(1S,4R)-4-hydroxymethylcyclopentan-1-yl]guanine.

* * * * *